United States Patent [19]

Petillo

[11] Patent Number: 4,940,468

[45] Date of Patent: Jul. 10, 1990

[54] APPARATUS FOR MICROSURGERY

[76] Inventor: Phillip J. Petillo, 1206 Herbert Ave., Ocean, N.J. 07712

[21] Appl. No.: 143,652

[22] Filed: Jan. 13, 1988

[51] Int. Cl.$^5$ .............................................. A61B 17/32
[52] U.S. Cl. ...................................... 606/170; 604/22
[58] Field of Search ...................... 604/22, 27, 35, 264; 128/305, 305.1, 752–755, 751, 321, 346; 433/118–120, 124; 92/165 PR, 177, 233; 606/167, 170, 180

[56] References Cited

U.S. PATENT DOCUMENTS

| | | |
|---|---|---|
| 1,677,209 | 7/1928 | Rose . |
| 2,703,557 | 3/1955 | Polki .................................... 92/177 |
| 3,173,414 | 3/1965 | Guillant . |
| 3,180,236 | 4/1965 | Beckett ................................ 92/177 |
| 3,614,953 | 10/1971 | Moss . |
| 3,776,238 | 12/1973 | Peyman et al. . |
| 3,815,604 | 6/1974 | O'Malley . |
| 3,828,791 | 8/1974 | Santos ................................ 128/321 |
| 3,884,238 | 5/1975 | O'Malley . |
| 3,994,297 | 11/1976 | Kopf . |
| 4,009,654 | 3/1977 | Freimuth ............................ 92/249 |
| 4,011,869 | 3/1977 | Seiler, Jr. . |
| 4,214,507 | 7/1980 | Hock et al. ......................... 92/249 |
| 4,577,629 | 3/1986 | Martinez . |
| 4,650,460 | 3/1987 | Roizenblatt . |

Primary Examiner—C. Fred Rosenbaum
Assistant Examiner—William Lewis
Attorney, Agent, or Firm—Michael B. Einschlag

[57] ABSTRACT

Apparatus for removing tissues such as vitreous humer from an eye has an outer needle having an aperture near one end; an inner tube disposed partially within the outer needle, having a sharp end and another end to which a vacuum is applied; a drive system for reciprocating the inner tube within the outer needle so that the sharp end of the inner tube reciprocates across the aperture to cut tissue; indexing means so that the inner tube does not rotate with respect to the outer needle; and venting means for releasing compressed air.

8 Claims, 12 Drawing Sheets

FIG. 8
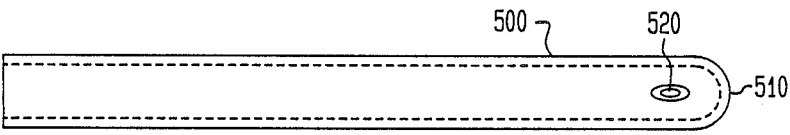
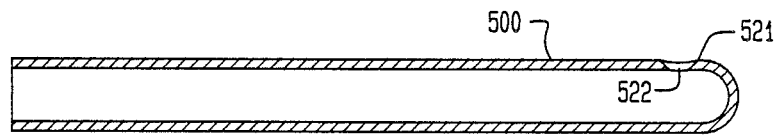
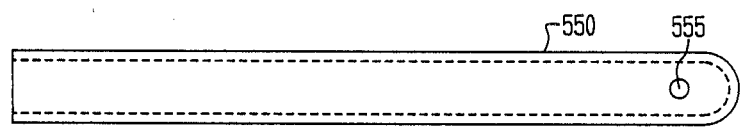

APPARATUS FOR MICROSURGERY

BACKGROUND OF THE INVENTION

1. Field of the Invention

The present invention pertains to apparatus for microsurgery and, in particular, to apparatus which is useful for intraocular surgery which includes removing vitreous from the eye.

2. Description of the Prior Art

The vitreous gel comprises seventy (70) percent of the eye weight and volume and is comprised of ninety-nine (99) percent water and one (1) percent of two main components, collagen fibers and hyaluronic acid, which are bound to large amounts of water. The vitreous owes its characteristic consistency to its sincicial structure in which long collage: chains form the frame for dispersion of hyaluronic acid molecules. This fact and the absence of blood vessels in the vitreous space guarantee the excellent light transmission properties and the inelasticity of the gel. Further, the external surface of the vitreous, called the hyaloid membrane, is a form of densified vitreous gel which is in contact with the following eye structures: the posterior capsule of the crystalline the pars plana epithelium, the retina and the optic nerve.

Alterations of the vitreous prevent light from being normally focused on the retina. Examples of such vitreous alterations are: vitreous bands causing traction and detachment of the retina; vitreous opacification due to the inflammatory or infectious process; the presence of foreign bodies in the vitreous space; eye perforations causing vitreous loss, vitreaous band formations; and many other circumstances. When a surgeon finds it necessary to remove diseased vitreous or other extraneous matter from within the eye, this removal must be accomplished without damage to the retina, to the optic nerva or to their associated blood vessels. This is no easy task as the vitreous cannot be cut by a scalpel or other similar instrumant because it is relatively tough and simply folds over the edge of the knife and refuses to be severed. It is known in the art that one can cut the vitreous gel mechanically using a method wherein two concentric needles, the inner one having a chopping, rotating or oscillating action against the outer tube, cut the vitreous gel and strands. After being cut, the severed vitreous is drawn inside the inner tube by way of suction and, in this way, is removed from the eye.

Many attempts have been made in the art to fabricate apparatus for removing portions of the vitreous humer and/or for cutting vitreous strands in vitreous hemorrhage in order to render the vitreous humer section of the eye transparent. One example of such an apparatus was disclosed in an article by G. A. Peyman and N. A. Dodich entitled "Experimental Vitrectomy," *Arch. Ophthal.*, Vol. 86, Nov, 1971, pp. 548-551 and U.S. Pat. No. 3,776,238 which issued Dec. 4, 1973. The apparatus disclosed in this article and patent consists of two concentric tubes, the outer tube having a hole in the sidewall which forms a mouth near a closed end of the outer tube. The apparatus cuts vitreous as a result of a chopping action of a sharp end of the inner tube against a plain end of the outer tube. The vitreous and strands which are trapped in the tube mouth are chopped and removed through the inner tube by suction applied thereto. The chopping action is caused by oscillating the inner tube within the outer tube, the oscillation being achieved by the action of a solenoid which is affixed to the inner tube. Further, as disclosed, the rate of oscillation of the chopping action can be varied between five and fifty times per second.

A further apparatus for surgically removing vitreous and the like from the eye is disclosed in U.S. Pat. No. 3,815,604 which issued on June 11, 1974. The push-cut apparatus comprises a cylinder having a pneumatically activated piston sliding therewithin. A cutting tube is rigidly fastened to the piston and passes therethrough to a debris-extracting tube. The cutting tube is positioned inside an outer tube and is free to slide therein between physical limits set by a cylinder head and a piston. A narrow slit in the inner tube extends for a considerable length along the tube from a sharp cutting edge. The slit permits the inner tube to be sprung out slightly so that the sharpened end of the inner tube is pressed tightly against the inner surface of the outer tube to ensure, thereby, a good shearing action when the sharp end of the inner tube passes a port opening in the outer tube. The apparatus further includes vent holes for the inside of the housing and means for preventing the piston from rotating with respect to a cap. Vitreous to be severed is drawn into the port opening of the outer tube by suction and is cut off when the piston moves the inner tube so that the sharp end thereof crosses the port of the outer tube. The frequency of traverse of the cutting end of the inner tube across the port of the outer tube is controlled by an electrical circuit which generates timed electrical pulses for controlling air pressure and suction pulses to the piston of the cutting device. This frequency of the pulses may be controlled by a foot-actuated device which is operated by a surgeon employing this apparatus.

A further apparatus for surgically removing vitreous and the like from the eye is disclosed in U.S. Pat. No. 3,884,238 which issued on May 20, 1975. The body or handle of the apparatus comprises a cylinder having a bellows disposed therein. A cutting tube having a sharp end is rigidly fastened to the bellows and is disposed inside an outer tube. The cutting tube is free to slide between physical limits which are manually adjustable. Vitreous to be severed is drawn into a port in the outer tube by suction. This vitreous is cut off when the sharp end of the inner cutting tube is moved across the port of the outer tube. The frequency of traverse of the sharp end of the inner tube across the port of the outer tube is controlled by an electrical circuit which generates timed electrical pulses for controlling air pressure and suction pulses to the piston of the apparatus. This frequency may be controlled by a foot-actuated device which is operated by the surgeon employing this instrument. Air pressure and vacuum are applied to the bellows of the apparatus through a flexible tube and a debris tube is positioned inside of the tube supplying pressure and vacuum.

A further ophthalmic instrument for surgically removing vitreous and the like from the eye is disclosed in U.S. Pat. No. 3,994,297 which issued on Nov. 30, 1976. The apparatus includes a cutting means formed from an inner tube which is slidably carried in an outer tube, i.e., the inner tube reciprocates inside the outer tube. Material to be excised enters a port in the outer tube and is sheared off by the inner tube. The excised material is then removed through the interior portion of the inner tube by a vacuum. The inner tube is rigidly carried by a piston which is driven, in turn, by a pneumatic driver. The pneumatic driver provides pulses of compressed air into a chamber to move the piston. The movement of the piston compresses a spring and the spring returns the piston to a neutral position when the air pulse is no longer present. The apparatus further includes an O-ring which slidably engages the inner tube in order to prevent the compressed air from escaping therein. The cavity between the inner tube O-ring and the piston is vented to the atmosphere by a passageway to avoid compressing air trapped between the inner tube O-ring and the piston. Further, vents are used to prevent compression of the air in the spring housing.

A further apparatus for surgically removing vitreous and the like from the eye is disclosed in U.S. Pat. No. 4,011,869 which issued on March 15, 1977. A resilient, inner tubular member is slidably mounted coaxially within a tubular housing. The tubular housing is bent to displace a cutting orifice in the side thereof in a direction toward the resiliant, inner tubular member. As one end of the resilient, inner tubular member passes across the cutting orifice, the inner member is resiliently urged into shearing contact with the cutting orifice. Vitreous matter which is to be severed is drawn into the cutting orifice by a vacuum applied through the inner diameter of the resilient, inner, tubular member. This vitreous matter, including tough fibrous matter approximately one micron thick, is severed by the end of the inner tube as it is driven by a piston across the cutting orifice. In addition, replacement saline solution is introduced into the eye through a further passageway and orifice to prevent collapse of the eyeball. The cutting surfaces of the cutting orifice and the end of the inner tube are inherently self-sharpening due to the resilient urging of one end of the inner tube against the orifice. Further, the self-sharpening effect is enhanced by fabricating the inner member from hard stainless steel and fabricating the tubular housing from fully annealed stainless steel.

A further apparatus for surgically removing vitreous and the like from the eye is disclosed in U.S. Pat. No. 4,577,629 which issued on March 25, 1986. The apparatus includes a cylindrical body having: (1) a vent passageway disposed at one end thereof; (2) front and rear plugs disposed in opposite ends thereof to mount a probe and evacuating and supply tubes; and (3) a piston disposed in a centrally located chamber therein to drive the probe. The front plug, disposed in the front end of the body, has an axial bore therethrough. The piston, disposed in the central chamber, is movable in a reciprocating manner toward and away from the front end; carries sealing rings therearound; and has an axial bore therethrough with a widened portion adjacent to the rear end of the piston. A spring, disposed in the body, engages the front end of the piston to bias the piston away from the front end of the body. The probe includes an elongate tubular outer member having a proximal end secured in the axial bore in the front plug, a closed distal end, and a port adjacent to the distal end. An elongate tubular inner member, slidably disposed in the outer member, has a portion fixed in the axial bore in the piston and a distal end movable across the port to provide a cutting action. The rear plug, disposed in the rear end of the body, has an axial bore therethrough aligned with the probe inner member to permit passage of cut material through the apparatus and a second bore therethrough communicating with the chamber for receiving pressure to move the piston and the probe inner member against the bias of the spring. Evacuating tube means communicates with the probe inner member and a source of suction to draw cut material through the probe inner member. Further, the apparatus can be utilized with any suitable source of suction communicating with the evacuating tube in any suitable pulsed source of pressurized fluid, preferably air, communicating with a supply tube. In addition, the apparatus is particularly well adapted for use with the Ocutome Model 8000 manufactured by CooperVision Incorporated which incorporates a source of suction and a source of pressure capable of supplying pressure pulses at an adjustable frequency of up to 400 pulses per minute or supplying a single pulse upon actuation of a switch to produce a single pulse which corresponds to a single cutting stroke. The suction supplied to the evacuating tube is controlled in conventional manner by a foot-hand operated device coupled with the source of suction.

As one can readily appreciate, the above-mentioned references disclose surgical outting instruments having a tubular outer member and a tubular inner member sliding therein and reciprocated by various means of motive power. These instruments have the disadvantages of not being economically disposable in that they include a number of intricate parts, require precision machining and tooling, require complicated assembly procedures and require disassembly for sharpening and sterilization.

There is a need for surgical outting instruments for cutting and removing vitreous, blood clots, cataracts, lenses and other matter from the eye, as well as for use in other microsurgical procedures. Further, there is a need for such a surgical instrument which: (1) is economically disposable; (2) is inexpensive to fabricate; (3) is easy to use; (4) provides precise cutting and adequate suction and evacuation of cut material; (5) provides a small amount of vibration; (6) is easy to operate; (7) is designed and shaped to facilitate manipulation by a surgeon; and (8) is reliable in operation.

SUMMARY OF THE INVENTION

Embodiments of the present invention solve the above-described problems in the prior art.

Surgical apparatus for removing tissue, including vitreous humer from an eye, comprises an outer needle having an aperture in the sidewall thereof; an inner tube disposed partially within the outer needle, having a sharp end and another end to which a vacuum is applied; a drive system for reciprocating the inner tube within the outer needle so that the sharp end of the inner tube reciprocates across the aperture to cut tissue which extends through the aperture; indexing means so that the inner tube does not rotate with respect to the outer needle, and venting means for releasing trapped compressed air.

Further specific embodiments include embodiments wherein the drive means comprises a piston which is driven by a source of compressed liquid or air and further: (1) the drive means comprises a multi-section piston wherein one of the sections has a smaller diameter than the barrel within which it reciprocates so that the piston: (a) does not have to be fabricated with tight tolerances and (b) does need further sealing apparatus such as, for example, an O-ring, to prevent leakage of compressed liquid or gas; (2) the indexing means comprises: (a) a groove disposed in the piston and an extension disposed in the barrel in which the piston reciprocates or (b) a piston having a shape which matches the shape of the inside of the barrel, both of which shapes are non-circular; and (3) the apparatus further comprises means for adjusting the position of the inner tube with respect to the aperture so that the size thereof may be adjusted.

Further specific embodiments include embodiments wherein the drive means comprises an electromagnetic drive means and further: (1) the drive means comprises: (a) a solenoid having a plunger disposed partially therein which is drawn into the solenoid when a current is applied thereto or (b) a magnetically attractive plunger which is drawn towards the solenoid when a current is applied thereto; (2) impact neutralizers to absorb energy from the impact of plunger; (3) the indexing means comprises: (a) a groove disposed in the plunger which rides along an extension disposed in the solenoid in which the piston reciprocates or (b) a plunger having a shape which matches the shape of the inside of the solenoid, both of which shapes are non-circular; and (4) the apparatus further comprises means for adjusting the position of the inner tube with respect to the aperture so that the size thereof may be adjusted.

BRIEF DESCRIPTION OF THE DRAWING

The principles of the present invention may be clearly understood by considering the following detailed description in conjunction with the accompanying drawing, in which:

FIG. 8 shows, in pictorial form, various outer needles having apertures which cooperate with inner tubes of embodiments of the present invention to provide a means for cutting tissue which extends into the aperture in the outer needle;

To facilitate understanding, identical reference numerals have been used to denote identical elements common to the figures.

DETAILED DESCRIPTION

Figure 1:
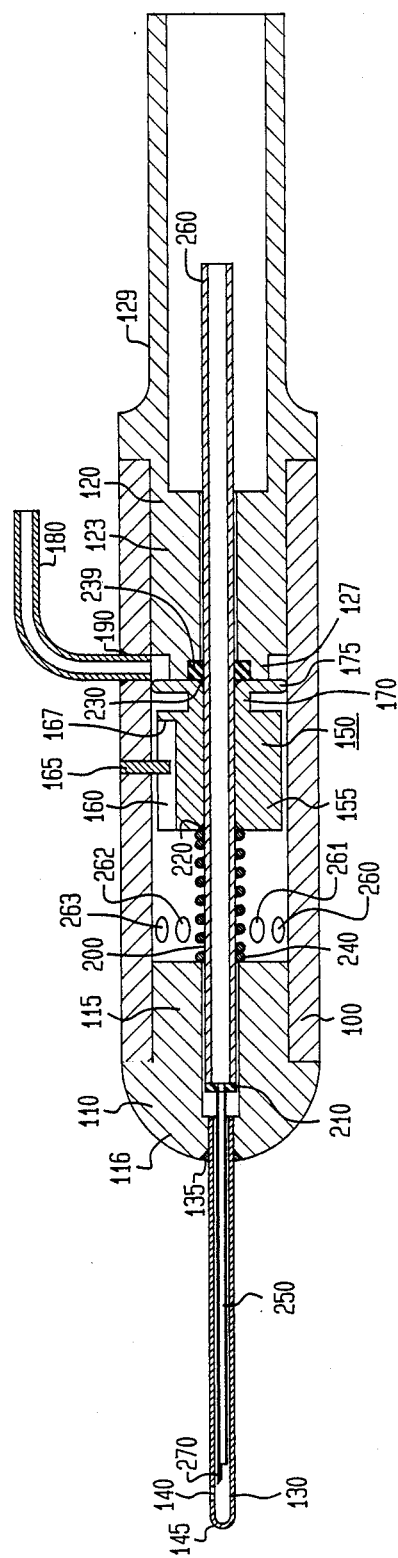
FIG. 1 shows, in pictorial form, a cross-section of an embodiment of the present invention having a pneumatic drive mechanism.

FIG. 1 shows a cross-section of an embodiment of the inventive apparatus, namely, a compressed liquid or gas-powered, intraocular, vitrectomy surgical needle 10. Barrel 100 of inventive apparatus 10 is a hollow tube having a substantially circular cross-section. However, the cross-section of the inside of barrel 100 need not be circular and, in fact, may have any one of a number of different shapes such as, for example, a substantially square cross-section. Barrel 100 may be fabricated from a sturdy plastic or a metal such as, for example, aluminum, and may have a knurled surface for ease of gripping.

Plug 110 is press-fit into barrel 100 and comprises cylindrical inner-plug-part 115 and outer-plug-part 116. Outer-plug-part 116 may have any one of many shapes and is shown in FIG. 1 to have a hemispherical shaped cross-section. Inner-plug-part 115 and outer-plug-part 116 have a passageway axially disposed through the center thereof. The passageway through outer-plug-part 116 has two parts, the first, left-hand passageway, as shown in FIG. 1, has a smaller diameter than the second, right-hand passageway. Further, the diameter of the right-hand passageway is substantially the same as the diameter of the passageway in inner-plug-part 115. The outer diameter of inner-plug-part 115 is substantially the same as the inner diameter of barrel 100. This ensures that plug 110 will be fixed in position when inner-plug-part 115 is press-fit into barrel 100.

Plug 120 is press-fit into the other end of barrel 100 from plug 110 and comprises cylindrical plug-part 123, recess-plug-part 127 and rear-portion 129. Cylindrical plug-part 123 and recess-plug-part 127 have a passageway axially disposed through the center thereof. The outer diameter of cylindrical plug-part 123 is substantially the same as the inner diameter of barrel 100. This ensures that plug 120 will be fixed in position when cylindrical plug-part 123 is press-fit into barrel 100. Rear-portion 129 has a relatively large passageway disposed therein and rear-portion 129 merely serves to provide support for a surgeon's hand.

It should be clear to those of ordinary skill in the art that plugs 115 and 120 may be affixed to barrel 100 by any one of a number of methods other than by being press-fit, for example, plugs 115 and 120 may be glued, wedged, or threadably received into barrel 100.

Outer needle 130 is inserted into the left-hand passageway in outer-plug-part 116 of plug 110 and is affixed therein by any one of a number of methods such as, for example, by glue inserted into outer-plug-part 116 at position 135 or by being press-fit and so forth. Outer needle 130 has a rounded end 145 which is disposed at the other end from its point of insertion into outer-plug-part 116. It should be clear to those of ordinary skill in the art that end 145 may have many different shapes, however, a rounded shape is preferred because it entails less damage to tissues when outer needle 130 is inserted into an eye. Aperture 140 is disposed in the sidewall of outer needle 130 near rounded end 145 thereof, but displaced a small distance therefrom towards outer-plug-part 116. Outer needle 130 is preferably a hypo-tube which is well-known in the art as a stainless steel tube but may also be fabricated from other materials such as, for example, plastic.

Drive-mechanism 150 is disposed within barrel 100 and comprises several sections. Drive-section 155 of drive 150 comprises a substantially cylindrical body fabricated, for example, from metal or plastic and has a passageway axially disposed through the center thereof. Although drive-section 155 need not be cylindrical, it is preferable that the shape of the cross-section of its outer surface match the shape of the cross-section of the inner surface of barrel 100.

Groove 160, extending downward from and along the outer surface of drive-section 155, cooperates with indexing-member 165 to provide indexing for drive-mechanism 150. As shown in FIG. 1, indexing-member 165 extends downwardly from the sidewall of barrel 100 and is inserted into groove 160 disposed in drive-section 155. Indexing-member 165 may be fabricated, for example, by fabricating a hole in the sidewall of barrel 100, fabricating threads in the hole, and threading a bolt therein which extends through the sidewall of barrel 100 and into indexing-groove 160 of drive-section 155. It should be clear to those of ordinary skill in the art that many other methods of affixing indexing-member 165 to a hole in the sidewall of barrel 100 may be used, such as, for example, by gluing. If indexing-groove 160 does not extend along the full length of drive-section 155, then end 167 of indexing-groove 160 may act as a stop for drive-mechanism 150. As a result of the above indexing configuration, drive-mechanism 150 does not rotate when it reciprocates within barrel 100.

Drive-mechanism 150 further comprises drive-section 170 which is disposed adjacent drive-section 155. Drive-section 170 has an axially disposed passageway extending therethrough which is substantially colinear with the passageway extending through drive-section 155. Further, the cross-section of the outer surface of drive-section 170 may have many different shapes, for example, a circular cross-section. However, the cross-section of the outer surface of drive-section 170 is preferably smaller than the cross-section of the outer surface of drive-section 155.

Drive-mechanism 150 further comprises drive-section 175 which is disposed adjacent drive-section 170. Drive-section 175 has an axially disposed passageway extending therethrough which is substantially colinear with the passageway extending through drive-sections 155 and 170. The cross-section of the outer surface of drive-section 175 should conform to the shape and size of the cross-section of the inner surface of barrel 100. Thus, for the embodiment shown in FIG. 1, drive-section 175 is cylindrical and has an outer diameter which is substantially the same as the inner diameter of barrel 100. As shown in FIG. 1, a space is formed between drive-sections 155 and 175 of drive-mechanism 150. While it is not necessary to fabricate drive-mechanism 150 so that this space is formed, i.e., drive-mechanism 150 may be fabricated without utilizing drive-section 170, the embodiment shown in FIG. 1 is a preferred embodiment. This is because the space formed as a result of fabricating drive-section 170 between drive-sections 155 and 175 allows drive-section 175 to flex when drive-mechanism 150 is reciprocated inside barrel 100. Due to this flexing action, the outer surface of drive-section 175 is made to conform to the inner wall of barrel 100 and, as a result, drive-mechanism 150 may advantageously be fabricated without requiring critical tolerances. Further, drive-mechanism 150 may advantageously be fabricated without utilizing a sealing apparatus such as an 0-ring for the purpose, as will be explained in detail below, of preventing compressed air from being forced around drive-mechanism 150, into any cf the tubes and, from there, into a patient's eye.

Figure 2:
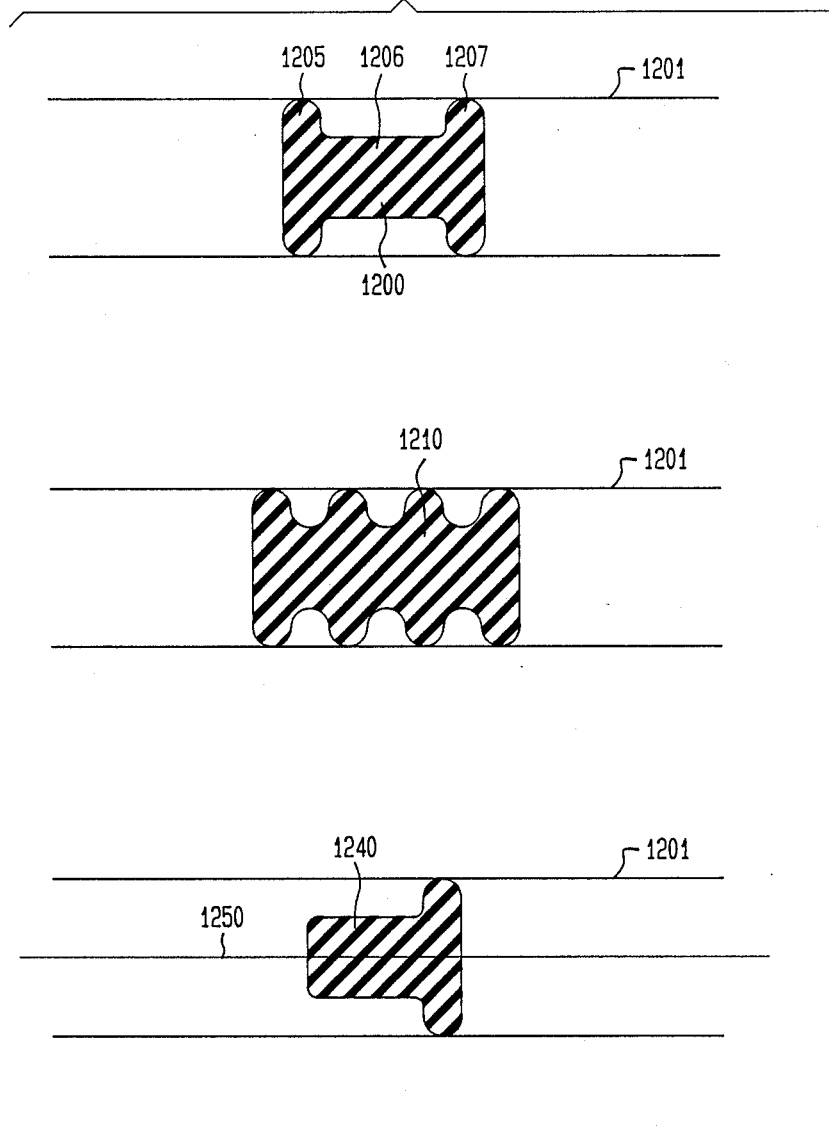
FIG. 2 shows, in pictorial form, various embodiments of drive-mechanisms for use with embodiments of the present invention.

It should be clear to those of ordinary skill in the art that inventive drive-mechanism 150 is useful for fabricating mechanisms which are powered by compressed liquids or gases such a air-powered cylinders. In such systems, drive-mechanism 150 will serve to be driven by a source of, for example, compressed air. Further embodiments of drive-mechanism 150 are shown in FIG. 2. Drive-mechanism 1200 is disposed in cylinder 1201; comprises sections 105, 1206 and 1207; and is adapted to be driven by compressed liquids or compressed gases toward the right and back toward the left. Further, the cross-section of the inside of cylinder 1200 and the outside of sections 1205 and 1207 need not be circular. In fact, they may have any one of a number of different shapes such as, for example, a hexagon, or a square and so forth, as long as they conform to each other. Still further, drive-mechanism 1210 is another embodiment thereof. Yet still further, embodiment 1240 may serve as a drive-mechanism when it rides on shaft 1250 disposed through the center thereof. Shaft 1250 serves to center drive-mechanism 1240 within cylinder 1201. It should be clear to those of ordinary skill in the art that a cross-section of the outside surface of the largest section of drive-mechanism sections 1200, 1210, and 1240 need not be circular but need only conform to the shape of the inside of cylinder 1201. Note, however, if the cross-section of the inner surface of cylinder 1201 is not circular, then indexing will be provided automatically so that a drive-mechanism disposed therein will not rotate.

Hollow, air-input-tube 180 is affixed to an aperture in the sidewall of barrel 100. Whenever a supply of pressurized fluid or gas, such as air, is affixed to one end of tube 180 (not shown), the liquid or gas is forced into barrel 100 and is forced against drive-section 175 of drive-mechanism 150. This drives drive-mechanism 150 toward the left, as shown in FIG. 1. Air-input-tube 180 is affixed to the side wall of barrel 100 by any one of a number of methods known in the art, for example, by gluing at points 190.

Tube 200 is disposed within barrel 100. Tube 200 is cylindrical in shape and has an outer diameter which is smaller than: (1) the inner diameter of the passageway in inner-plug-part 115; (2) the inner diameter of the right-hand passageway in outer-plug-part 116; and (3) the inner diameter of the passageway in plug 120. Further, the outer diameter of tube 200 is substantially the same as the inner diameter of the axially disposed passageway passing through drive-mechanism 150. Tube 200 is affixed to drive-mechanism 150 by any one of a number of methods known in the art, for example, by gluing or by being press-fit and so forth.

Figure 3:
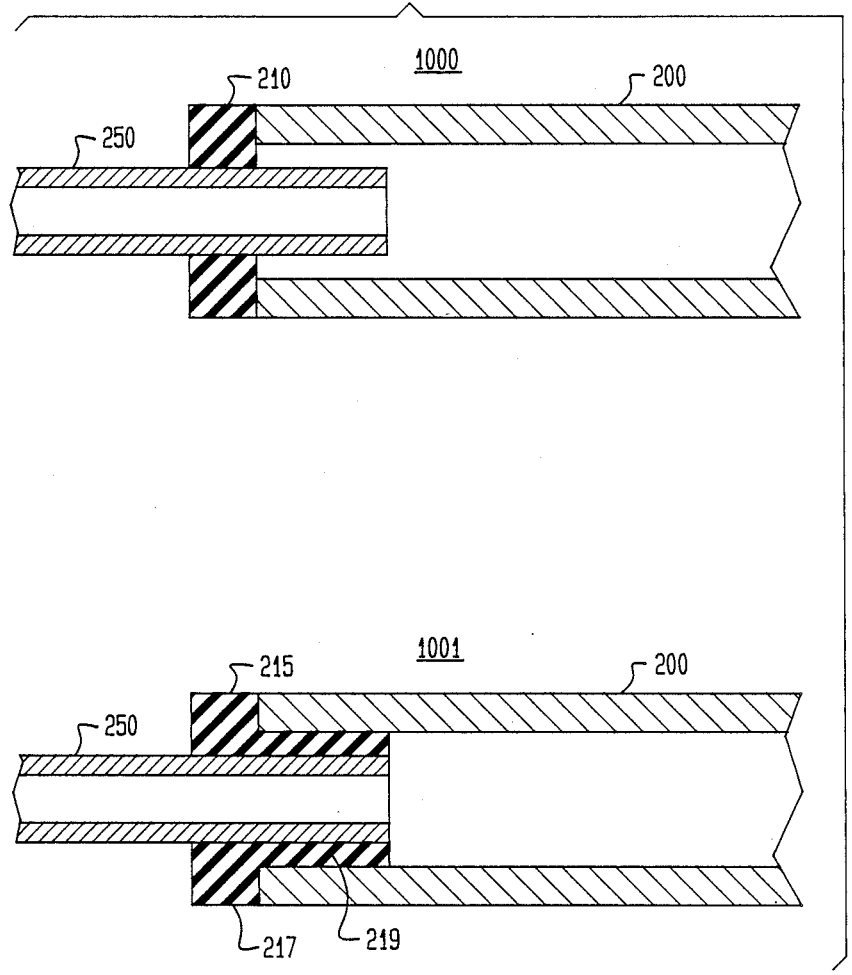
FIG. 3 shows, in pictorial form, two methods of impact neutralization for use in the embodiments of the present invention.

FIG. 3 shows two methods for affixing tube 200 to tube 250 and for providing an impact neutralizer for tube 200 within plug 110 as it reciprocates, as will be explained in detail below, within barrel 100. As shown in embodiment 1000 of FIG. 3, tube 250 extends into tube 200 and is affixed in that position by any one of a number of methods known in the art such as, for example, by being press-fit. In embodiment 1000, the outer diameter of tube 250 is substantially the same as the inner diameter of tube 200. Impact neutralizer means 210, for example, a washer, an O-ring, and so forth, surrounds tube 250 and has an outer diameter which is: (1) substantially the same as or smaller than the inner diameter of the right-hand passageway of outer-plug-part 116; (2) larger than the inner diameter of the left-hand passageway of outer-plug-part 116; and (3) larger than the inner diameter of tube 200. Thus, when tube 200 is driven to the left, its motion in that direction is stopped: (1) by the narrowed opening of the left-hand passageway in outer-plug-part 116 or (2) by indexing-member 165 impacting on groove-end 167. If the motion of tube 200 is stopped by plug 110, impact neutralizer 210 absorbs energy from tube 200 whenever an end thereof impacts outer-plug-part 116.

As shown in embodiment 1001 of FIG. 3, tube 250 extends into impact neutralizer 215 which, in turn, is affixed to tube 250. Impact neutralizer 215 is formed from any energy-absorbing material and comprises two sections having a passageway axially disposed through the center thereof, outer-impact-part 217 and inner-impact-part 219. In embodiment 1001, outer-impact-part 217 and inner-impact-part 219 are cylindrical and inner-impact-part 219 is affixed to tube 200, by being press-fit thereinto. The outer diameter of inner-impact-part 219 is substantially the same as the inner diameter of tube 200 and the inner diameter of outer-impact-part 217 and inner-impact-part 219 are substantially the same as the outer diameter of tube 250. The outer diameter of outer-impact-part 215 is: (1) substantially the same as or smaller than the inner diameter of the right-hand passageway of outer-plug-part 116; (2) larger than the inner diameter of the left-hand passageway of outer-plug-part 116; and (3) larger than the inner diameter of tube 200. Thus, when tube 200 is driven to the left, its motion in that direction is stopped by the narrowed opening of the left-hand passageway in outer-plug-part 116 and impact neutralizer 215 absorbs energy from tube 200 whenever, or if, an end thereof impacts outer-plug-part 116.

Tube 200 is affixed to drive-mechanism 150 by, for example, gluing at point 220 at one end of drive-section 155 and at point 230 at one end of drive-section 175. Tube 200 may also be swaged to tube 250. Tube 200 extends through the end of barrel 100 and through the end of rear plug 120. The outer diameter of tube 200 is smaller than the inner diameter of the passageway disposed in rear plug 120. Thus, when drive mechanism 150 is forced to the left by pressurized air entering barrel 100 through air-input-tube 180, tube 200 is also driven to the left because it is affixed to drive-mechanism 150 in the manner described above. Further, tube 200 is driven within the passageways disposed in plugs 110 and 120 because the outer diameter of tube 200, as described above, is smaller than the inner diameter of the passageways disposed within these two plugs.

The outer diameter of recess-plug-part 127 of plug 120 is substantially less than the inner diameter of barrel 100 to provide a chamber in barrel 100 into which pressurized air enters from air-intake-tube 180. The inner diameter of the passageway in recess-plug-part 127 is larger than the outer diameter of tube 200 which extends therethrough. Seal 239, disposed in the passageway in recess-plug-part 127, is formed from a relatively soft material such as, for example, urethane or silicone, to prevent pressurized air that enters barrel 100 from leaking out through plug 120.

Spring return 240 is disposed along tube 200 between inner-plug-part 115 of plug 110 and drive-section 155 of drive-mechanism 150. As a result, spring 240 is compressed when drive-mechanism 150 is driven to the left when pressurized air enters barrel 100 from air-input-tube 180. When pressurized air ceases to flow through air-input-tube 180 and, thereby, against one side of drive-section 175 of drive-mechanism 150, spring 240 forces drive-mechanism 150 back toward the right, as shown in FIG. 1. Impact neutralizer means 210 absorbs energy if drive-mechanism 150 causes tube 200 to impact upon impact neutralizer 210 and outer-plug-part 116 and, thereby, reduces any noise and vibration that occurs therewith.

Tube 250, for example, hypo-tube in stainless steel or plastic, is substantially cylindrical in shape, has an outer diameter which is smaller than the inner diameter of outer needle 130. Further, as has been described above, tube 250 is affixed to tube 200 by any one of a number of methods such as, for example, by being press-fit, by being push-fit thereinto, or by being swaged together. Because tube 250 is affixed to tube 200, as is evident from FIG. 1, as drive-mechanism 150 is driven to the left by pressurized air which enters barrel 100 from air-input-tube 180, so too is tube 250 driven to the left. Further, when drive-mechanism 150 is driven to the right when spring 240 expands, so too is tube 250 driven to the right. As a result, tube 250 undergoes reciprocating motion along the inside of outer needle 130.

A means for creating a vacuum is affixed to tube 200 at rear end 260 thereof. The means for creating a vacuum is not shown but such means are well-known to those of ordinary skill in the art. As a result, as is evident from FIG. 1, whenever a vacuum is applied to rear end 260 of tube 200, that vacuum is, in turn, applied through tube 200, through tube 250 and out of an opening in the end of tube 250 to the end of outer needle 130. Further, as shown in FIG. 1, one end of tube 250 includes cutting edge 270 which is disposed to slide along the surface of the inside wall of outer needle 130. In addition, tube 250 is disposed so that cutting edge 270 will be carried back and forth across aperture 140 in outer needle 130 when tube 250 is reciprocated therewithin.

In operation, the inventive apparatus shown in FIG. 1 functions as follows. A vacuum is applied to rear end 260 of tube 200. As described above, the vacuum is transmitted through tube 200 to tube 250 and, finally, through tube 250 to aperture 140 in outer needle 130. Outer needle 130 is inserted into the vitreous portion of an eye through an incision made in the cornea thereof. The vacuum causes vitreous tissue to be drawn into outer needle 130 through aperture 140. An operator then causes a source of compressed air to be applied to air-input-tube 180. Then, compressed air enters barrel 100 and drives drive-mechanism 150 to the left. As a result, cutting edge 270 of tube 250 is driven across aperture 140 and, thereby, slices off a bit of the tissue which extends through aperture 140 into outer needle 130. preferably, the movement of drive-mechanism 150 to the left should extend sufficiently far that cutting edge 270 of tube 250 is driven past the left-most extent of aperture 140. This will ensure proper scissoring action to slice the tissue cleanly off. The vacuum applied through rear end 260 of tube 200 then causes this tissue to be drawn through the tubes and into a collecting means, not shown.

Barrel 100 contains exhaust ports 260 to 263 which vent air that is compressed by the reciprocating motion of drive-mechanism 150 within barrel 100. Exhaust ports 260 to 263 prevent compressed air from: (1) being forced into any of the tubes and, therefrom, into the eye and (2) resisting the motion of drive-mechanism 150 to the left. Still further, exhaust ports 260 to 263 help prevent any build up of heat in apparatus 10.

Figure 4:
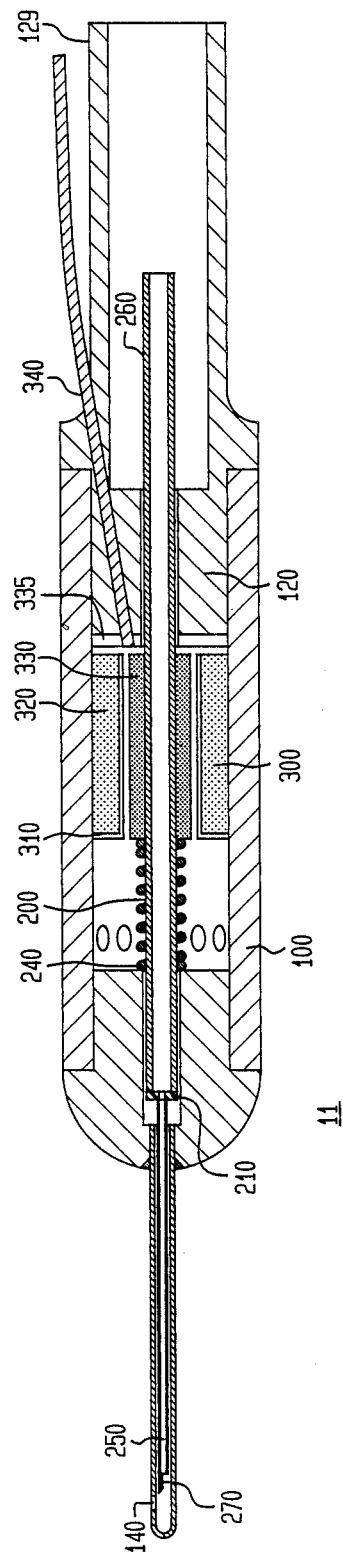
FIG. 4 shows, in pictorial form, a cross-section of a first embodiment of the present invention having an electromagnetic drive mechanism.

FIG. 4 shows a cross-section of another embodiment of the present invention, namely an electromagnetically-powered, intraocular, vitectomy surgical needle 11, which is similar in many respects to apparatus 10 shown in FIG. 1. However, the drive system for the embodiment shown in FIG. 4 comprises an electromagnetic drive system whereas the drive system for the embodiment shown in FIG. 1 is a compressed liquid or gas drive system. Specifically, in FIG. 4, drive-mechanism 300 comprises bobbin 310 having wires 320 wound therearound and a passageway axially disposed in the center thereof. In this embodiment, tube 260 is comprised of a substantially non-magnetic material such as, for example, aluminum or plastic, to prevent tube 260 from sticking to bobbin 310 and to improve efficiency. Magnetic-structure 330, for example, a steel cylinder, is affixed to the outside of a portion of tube 260 and the outer diameter of magnetic-structure 330 is smaller than the diameter of the passageway disposed within bobbin 310 of drive-mechanism 300. Indexing means (not shown) for magnetic-structure 330 are discussed below. Spring 240 is disposed against one end of magnetic-structure 330 and has an outer diameter which is smaller than the outer diameter of magnetic-structure 330. When no current is applied to wires 320 and spring 240 is not compressed, magnetic-structure 330 is disposed so that a portion thereof extends outside of the passageway in bobbin 310 to the right towards rear plug 120. Wire 320 is wrapped around bobbin 310 and is extended through aperture 340 in plug 120 to a supply of electric current, which supply is well known in the art and not shown in FIG. 4. Impact neutralizer means 335, formed from an energy absorbing material such as, for example, a soft washer, is disposed adjacent rear plug 120 to absorb energy from magnetic-structure 330 if it strikes rear plug 120 when magnetic-structure 330 reciprocates within barrel 100 and impact neutralizer means 210 acts, as was discussed above with respect to the embodiment shown in FIG. 1, to absorb energy if tube 260 strikes front plug 110. The inner diameter of impact neutralizer means 335 is larger than the outer diameter of tube 260 but is smaller than the outer diameter of magnetic-structure 330.

When electric current is applied to wire 320, a magnetic field is set up inside bobbin 310 and magnetic-structure 330 is attracted thereinto. As a result, magnetic-structure 330 moves toward the left in FIG. 4. This movement drives tube 250 to the left and compresses spring 240. When current is removed from wire 320, the magnetic field set up within bobbin 310 fades and spring 240 pushes magnetic-structure 330 and, thereby, tube 250 to the right. This above-described movement drives sharp, cutting edge 270 of tube 250 across aperture 140, thereby cutting off any vitreous material which extends into aperture 140 as a result of a vacuum being applied to end 260 of tube 200.

In the embodiment shown in FIG. 4, indexing to prevent tube 250 from rotating with respect to outer needle 140 is provided in any one of a number of ways. For example, in one embodiment the cross-section of the outer surface of magnetic-structure 330 may be fabricated to have a non-circular shape such as, for example, a hexagon, a square and so forth, and the passageway disposed within bobbin 330 is then fabricated to have the same shape. In other embodiments, a groove may be disposed within magnetic-structure 330 and a member may be fabricated on bobbin 310 which extends into the groove.

Figure 5:
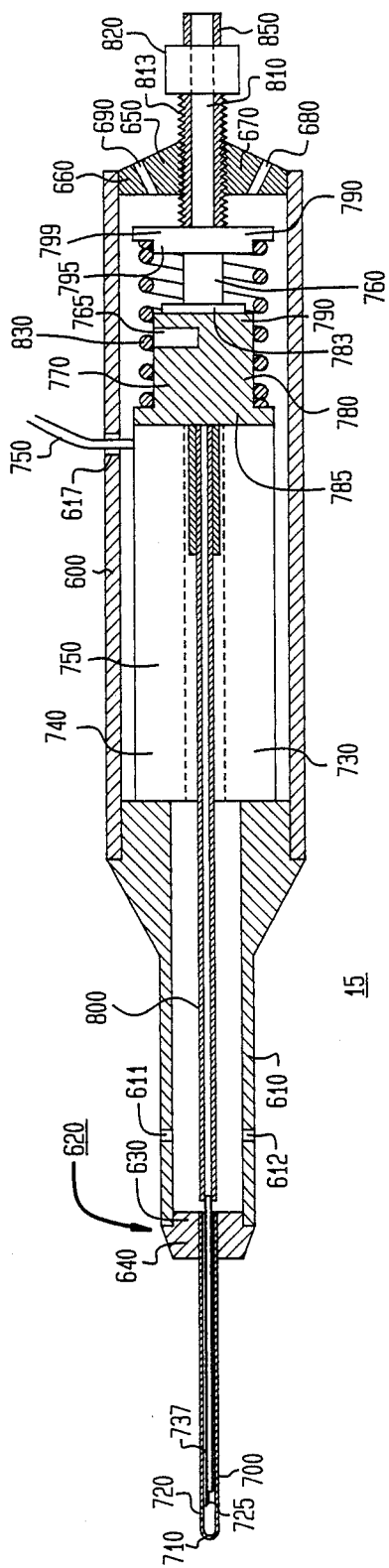
FIG. 5 shows, in pictorial form, a cross-section of a second embodiment of the present invention having an electromagnetic drive mechanism.

FIG. 5 shows a cross-section of a further embodiment of the present invention which comprises an electromagnetic drive system. Barrel 600 of inventive apparatus 15 is a hollow tube having a substantially circular cross-section. However, the cross-section of the inside of barrel 600 need not be circular and, in fact, may have any one of a number of different shapes such as, for example, a substantially square or hexagonal cross-section. Barrel 600 may be fabricated from a sturdy plastic or a metal such as, for example, aluminum, and may have a knurled surface for ease of gripping. Further, barrel 610, a hollow tube, like barrel 600, is affixed to barrel 600 by, for example, being press-fit thereinto, and has a smaller outside diameter than barrel 600. Although barrel 610 is not necessary for operation of the apparatus, it provides a preferred embodiment because barrel 610 substantially improves a surgeon's ability to grip and use the inventive apparatus. Barrel 610 has vents 611 and 612 disposed in the sidewall thereof which prevent any compressed air from being forced into outer needle 700 and, from there, into a patient's eye. Further, vents 611 and 612 prevent any heat build-up in apparatus 15.

Plug 620 is press-fit into barrel 610 and comprises cylindrical inner-plug-part 630 and outer-plug-part 640. Outer-plug-part 640 may have any one of man shapes and is shown in FIG. 5 to have a trapezoidally shaped cross-section. Inner-plug-part 630 and outer-plug-part 640 have a passageway axially disposed through the center thereof. The outer diameter of inner-plug-part 630 is substantially the same as the inner diameter of barrel 610. This ensures that plug 620 will be fixed in position when inner-plug-part 630 is press-fit into barrel 610. It should be clear to those of ordinary skill in the art that further embodiments of the present invention include embodiments wherein plug 620 and barrel 610 are fabricated as a single piece.

Plug 650 is press-fit into the end of barrel 600 which is opposite from barrel 610 and comprises a cylindrical inner-plug-part 660 and outer-plug-part 670. Outer-plug-part 670 may have any one of many shapes and is shown in FIG. 5 to have a triangularly shaped cross-section. Inner-plug-part 660 and outer-plug-part 670 have a passageway axially disposed through the center thereof and have several, smaller apertures, for example, 680 and 690, disposed therethrough which serve, as will be explained in further detail below, as vents. The outer diameter of inner-plug-part 660 is substantially the same as the inner diameter of barrel 600. This ensures that plug 650 will be fixed in position when plug 650 is press-fit into barrel 600. It should be clear to those of ordinary skill in the art that plug 620 may be affixed to barrel 610 and that plug 650 may be affixed to barrel 600 by any one of a number of methods other than by being press-fit, for example, plugs 620 and 650 may also be glued, wedged, or threadably received into barrels 610 and 600, respectively. Further, it should be clear to those of ordinary skill in the art that further embodiments of the present invention include embodiments wherein plug 650 and barrel 600 are fabricated as a single piece.

Outer needle 700 is inserted into plug 620 and is affixed therein by any one of a number of methods such as, for example, by gluing or by being press-fit and so forth. In fact, outer needle 700 may even extend through plug 620 and into the passageway disposed within barrel 610. Outer needle 700 has a rounded end 710 which is disposed at the other end from its point of insertion into plug 620. It should be clear to those of ordinary skill in the art that end 710 may have many different shapes, however, a rounded shape is preferred because it entails less damage to tissues when outer needle 700 is inserted into an eye. Aperture 720 is disposed in the sidewall of outer needle 700 near the rounded end thereof, but displaced a small distance therefrom towards plug 620. Outer needle 700 is preferably a hypo-tube which is well-known in the art as a stainless steel tube but may also be fabricated from other materials such as, for example, plastic.

Inner tube 737 is disposed within outer needle 700 and has an outer diameter which is smaller than the inner diameter of outer needle 700. Tube 737 has sharp, cutting edge 725 disposed at one end and the other end extends through the passageway in plug 620 and is affixed to tube 800 by any one of a number of methods such as, for example, by being press-fit. The outer diameter of tube 737 is substantially the same as the inner diameter of tube 800.

Drive-mechanism 730 is disposed within barrel 600 and comprises several sections. These sections include bobbin 740 which has a passageway axially disposed in the center thereof and wires 750 wound therearound. Wires 750 extend through aperture 617 in barrel 600 to a supply of electric current, which supply is well known in the art and not shown in FIG. 5. Tube 800 extends through the passageway in bobbin 740 and is comprised of a substantially non-magnetic material such as, for example, aluminum, to prevent tube 800 from sticking to bobbin 740. Magnetic-structure 760, for example, a steel cylinder or slug of steel, is affixed to the outside of a portion of tube 800. The outer diameter of magnetic-structure 760 is smaller than the diameter of the passageway disposed within bobbin 740 of drive-mechanism 730. It should be clear to those of ordinary skill in the art that drive-mechanism 730 typically has a ferrous slug (not shown for clarity) disposed in the front end of bobbin 740. This slug is so disposed that magnetic-structure 760 would be attracted thereto when current is applied to wires 750. Magnetic-structure 760 further comprises pin-member 765 which extends outward from the outer surface thereof. Pin-member 765 may be fabricated by any one of a number of methods such as, for example, by drilling and tapping a hole in magnetic-structure 760 and threading a bolt therein, by drilling a hole in magnetic-structure 760 and press-fitting a bolt therein and so forth.

Magnetic-structure 760 is further affixed to spring-containment-means 799, which spring-containment-means 799 comprises a first cylindrical section 795 and a second cylindrical section 790. First and second cylindrical sections 790 and 795 have a passageway disposed axially through the center thereof and the diameter of the outer surface of a cross-section of cylindrical section 790 is larger than that of cylindrical section 795 so that a ledge is formed therebetween.

Indexing means 770 comprises first and second cylindrical sections 780 and 785 and is affixed to bobbin 740. First and second cylindrical sections 780 and 785 have a passageway disposed axially through the center thereof whose diameter is greater than the diameter of a cross-section of the outer surface of magnetic-structure 760. The diameter of the outer surface of a cross-section of cylindrical section 785 is larger than that of cylindrical section 780 so that a ledge is formed therebetween. A groove is disposed along the inner surface of the passageway in cylindrical section 780. Pin-member 765 of magnetic-structure 760 is disposed to extend into the groove in the inner surface of the passageway in cylindrical section 780 to provide an indexing means which prevents the rotation of magnetic-structure 760 when it reciprocates within apparatus 15 and, thereby, the rotation of tube 737 relative to outer needle 700. In the embodiment shown in FIG. 5, indexing to prevent tube 737 from rotating with respect to outer needle 700 may also be provided in any one of a number of other ways. For example, in one embodiment, the cross-section of the outer surface of magnetic-structure 760 may be fabricated to have a non-circular shape such as, for example, a hexagon, a square and so forth, and the passageway disposed within bobbin 740 is then fabricated to have the same shape.

Impact neutralizer means 783 is affixed to indexing means 770 and is fabricated from an energy absorbing material such as, for example, urethane, plastic, silicone, and so forth. Impact neutralizer means absorbs energy whenever spring-containment-means 799 impacts thereon.

Adjusting means 810 is disposed against one side of spring-containment means 799. The distance between the end of bobbin 740 and the far end of magnetic-structure 760 is adjustable and is determined by the position of adjusting means 810. Adjusting means 810 has a passageway axially disposed through the center thereof and tube 800 extends therethrough. In the embodiment shown in FIG. 5, adjusting means 810 comprises threaded rod 813 which is threaded into rear plug 650. Further, knob 820, affixed to the end of threaded rod 813, has a passageway axially disposed through the center thereof and tube 800 extends therethrough. As knob 820 is rotated, threaded rod 813 of adjusting means 810 is threaded into or out of barrel 600 and, thereby, the distance between the end of bobbin 740 and the far end of magnetic-structure 760 is decreased or increased. As one can readily appreciate by examining FIG. 5, since magnetic-structure 760 is affixed to tube 800, as the distance between the far end of magnetic-structure 760 and an end of bobbin 740 is decreased, tube 800 moves to the left in FIG. 5. In turn, cutting edge 725 of tube 737 moves to the left and this has the effect of decreasing the opening in aperture 720.

Coiled spring 830 is disposed about magnetic-structure 760, cylindrical section 780 and cylindrical section 795, the outer diameters of cylindrical sections 780 and 795 being substantially the same as the inner diameter of coiled spring 830. In its relaxed position, coiled spring 830 holds spring-containment-means 799 substantially against rod 810.

A means for creating a vacuum is affixed to tube 800 at the rear end 850 thereof. The means for creating a vacuum is not shown but such means are well-known to those of ordinary skill in the art. As a result, as is evident from FIG. 5, whenever a vacuum is applied to rear end 850 of tube 800, that vacuum is, in turn, applied through tube 800, through tube 737 and out of an opening in the end of tube 737 to aperture 720 in outer needle 700. Further, as shown in FIG. 5, one end of tube 737 includes cutting edge 725 which is disposed to slide along the surface of the inside wall of outer needle 700. In addition, tube 737 is disposed so that cutting edge 725 will be carried back and forth across aperture 720 in outer needle 700 when tube 737 is reciprocated therewithin.

In operation, inventive apparatus 15 shown in FIG. 5 functions as follows. A vacuum is applied to rear end 850 of tube 800. As described above, the vacuum is transmitted through tube 800 to tube 737 and, finally, through tube 737 to aperture 720 in outer needle 700. Outer needle 700 is inserted into the vitreous portion of an eye through an incision made in the cornea thereof. The vacuum causes vitreous tissue to be drawn into outer needle 700 through aperture 720. An operator then causes a current to be applied to wires 750 and a magnetic field arises in bobbin 740 in response thereto. Magnetic-structure 760 is attracted to the left by the magnetic field and moves toward bobbin 740. This movement drives tube 800 to the left and compresses coiled spring 830. Finally, cutting edge 725 of tube 737 is driven across aperture 720 and, thereby, slices off a bit of the tissue which extends through aperture 720 into outer needle 700. Preferably, the movement of magnetic-structure 760 to the left should extend sufficiently far that cutting edge 725 of tube 737 is driven past the left-most extent of aperture 720. This will ensure proper scissoring action to slice the tissue cleanly off. The vacuum applied through rear end 850 of tube 800 then causes this tissue to be drawn through the tubes and into a collecting means, not shown.

When current is removed from wires 740, the magnetic field set up within bobbin 740 fades and coiled spring 830 pushes magnetic-structure 760 and, thereby, tube 800 to the right. Impact neutralizer 783 absorbs energy when spring-containment-means 799 is pulled to the left as magnetic-structure 760 is drawn into bobbin 740. This reduces the noise and vibration attendant with the use of apparatus 15.

The maximum opening of aperture 720 is determined by adjusting means 810. As adjusting means 810 forces spring-containment-means 799 to the left, the right-most position of cutting edge 725 is forced further to the left. This reduces the maximum opening in aperture 720.

I have found that I can increase the power of the action of the magnetic field emanating from solenoid 730 by wrapping it with more than one wire, for example, two separate wires, and by applying current to each of the wires. For example, in a preferred embodiment, I have applied current to the wires in parallel by wrapping each end of the two wires together to form two connected ends and then by applying current simultaneously to the two ends.

Figure 10:
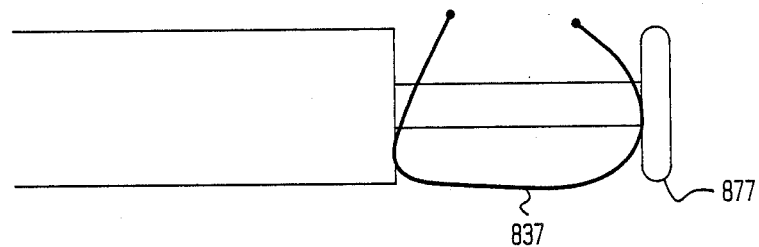
FIG. 10 shows, in pictorial form, an embodiment of a flat spring for use with embodiments of the present invention

Although spring 830 has been shown to be a coiled spring, many other embodiments may be used such as, for example, a wave washer or a flat spring and so forth. For example, one such embodiment using spring 837 is shown in FIG. 10. It should be clear to those of ordinary skill in the art that spring 837 is compressed as plunger 877 moves to the left. It should also be clear that spring 837 will force plunger 877 to the right when the force drawing it to the left is removed.

In a variation of the embodiment of the present invention which was shown in FIG. 5, coiled spring 830 may be affixed to spring-containment-means 799 but disposed between spring-containment-means 799 and plug 650. In this variation, when magnetic-structure 760 is drawn into bobbin 740 as current is applied to wires 750, spring 830 would be compressed. Then, when the current is removed, spring 830 would pull magnetic-structure 760 to the right. It should be clear to those of ordinary skill in the art that many other suitable arrangements may be fabricated utilizing a spring, all of which are within the spirit of the present invention.

Figure 6:
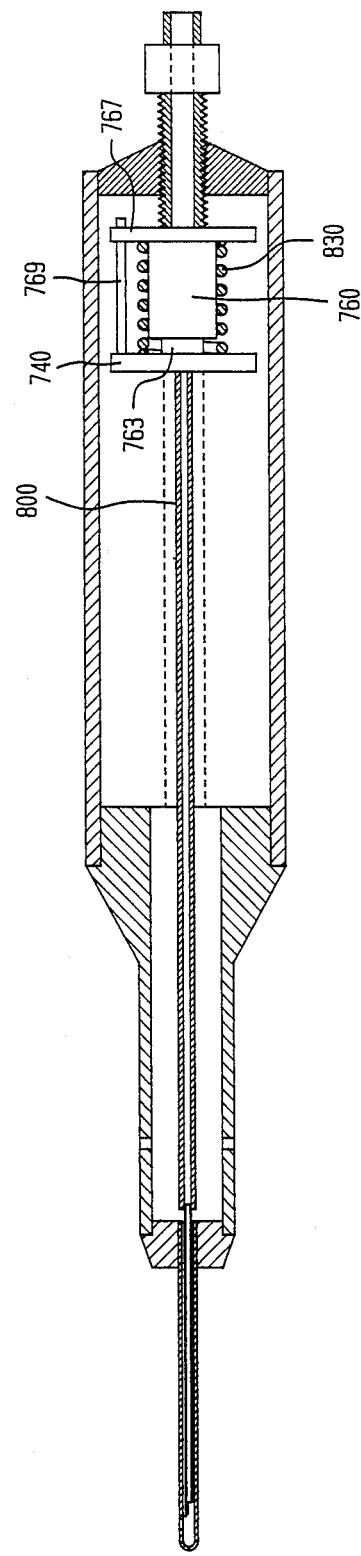
FIG. 6 shows, in pictorial form, a cross-section of a third embodiment of the present invention having an electromagnetic drive mechanism.

In a further embodiment of the present invention shown in FIG. 6, magnetic-structure 760 is affixed to tube 800. The cross section of magnetic-structure 760 is larger than the inner diameter of the passageway through bobbin 740. Soft bumper 763 is affixed to one end of magnetic-structure 760 and indexing-washer 767 having a larger cross-section than magnetic-structure 760 is affixed to the other end. Indexing-rod 769 is affixed to and extends outward from bobbin 740 through an aperture in indexing-washer 767. When current is applied to wires 750, a magnetic field arises which attracts magnetic-structure 760 towards bobbin 740 and compresses coiled spring 830. When the current is removed from wires 750, the magnetic field fades and coiled spring 830 pushes indexing-washer 767 and, thereby, magnetic-structure 760 back towards the right. As magnetic structure 760 reciprocates, indexing-rod 769 prevents rotation and bumper 763 prevents vibration.

A still further embodiment of the present invention which utilizes an electromagnetic drive system comprises the use of a linear motor.

Figure 7:
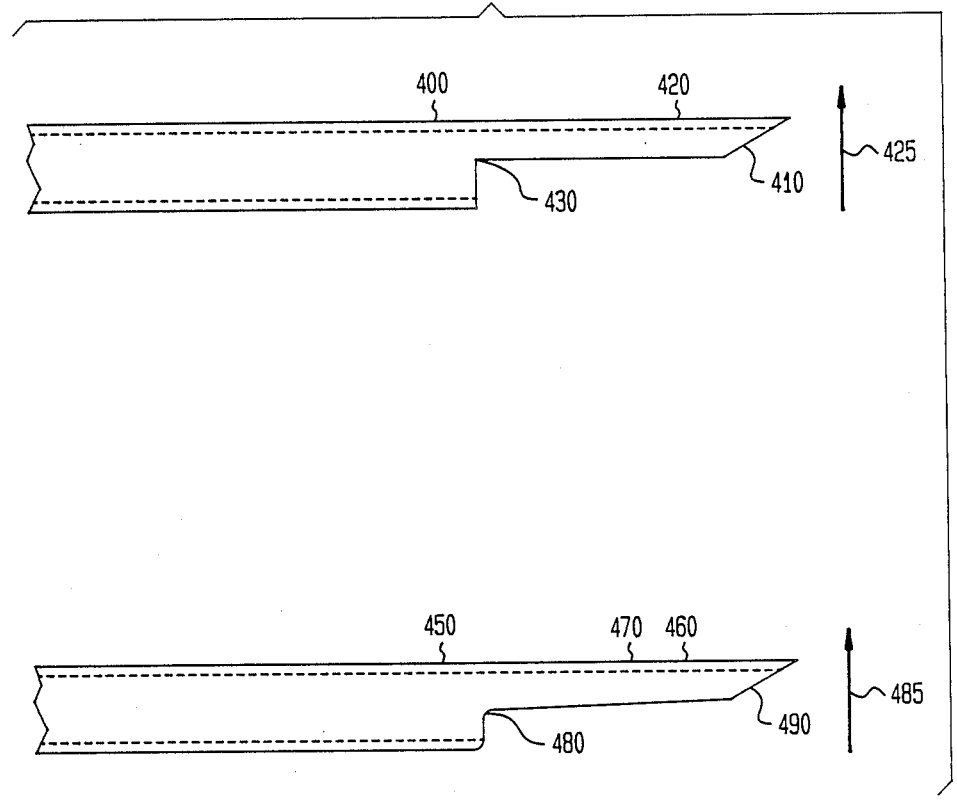
FIG. 7 shows, in pictorial form, a cross-section of an inner cutting tube for use with embodiments of the present invention.

FIG. 7 shows a prior art tube 400 which corresponds to tube 250 of FIGs. 1 and 4 and tube 737 of FIG. 5. Tube 400 includes end 410 which is sharpened and which can cut material which extends through aperture 140 of outer needle 130 of FIGS. 1 and 4 and aperture 720 of outer needle 700 of FIG. 5. In the prior art, section 420 of tube 400 was bent upward along the direction of arrow 425 so that an edge of end 410 can scrape along an inside wall of an outer needle to provide a scissoring action and, thereby, a better cutting edge. Unfortunately, as a result of this, cracks are created in tube 400 due to metal fatigue. Inventive tube 450 advantageously overcomes these deficiencies in the following manner: (1) section 460 is bent up slightly in the direction of arrow 485, for example, by 0.005", to again provide a scissoring effect along the inside of an outer needle; (2) section 460 is tapered so that a larger amount of metal exists at portion 470 of tube 450 than existed in prior art tube 400 in order to prevent fatigue; and (3) edge 480 is rounded to provide a means for releasing fatigue. Further, in order to provide an inexpensive means for fabricating the inventive apparatus, cutting edge 490 of inventive tube 450 is ground in one pass on a surface grinder using a grinding wheel having the shape of the cutting edge.

FIG. 8 shows two embodiments for fabricating the aperture in the side wall of tube 500 which corresponds to outer needle 130 of FIGS. 1 and 4 and outer needle 700 of FIG. 5. In first embodiment 500, shown in views 1 and 2, an ellipse 520 is ground near rounded edge 510. A cross-section of ellipse 520 is shown in view 2. Top edge 521 is blunt whereas bottom edge 522, which extends to the inner wall of tube 500, is sharp. Tube 550 is a further embodiment of an outer needle which has round aperture 550 drilled in the sidewall thereof. In fact, the aperture in the outer needle used in embodiments of the present invention may be oval, rectangular, diamond-shaped and so forth. Further, the aperture can be sharpened, as shown by sharp edge 522 of tube 500, or it can be blunt. Nevertheless, I have determined that a preferred embodiment comprises an ellipsoidally shaped aperture 520.

Figure 9:
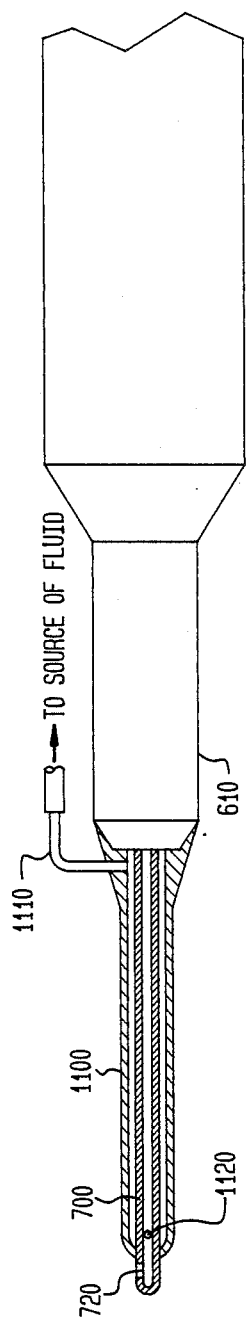
FIG. 9 shows, in pictorial form, an infusion sleeve for use with embodiments of the present invention.

FIG. 9 shows, in pictorial form, a cross-section of an infusion sleeve available in the prior art for us with embodiments of the present invention. Infusion sleeve 1100 is affixed at one end to outer needle 700 and at the other end to barrel 610. Infusion sleeve 1100 may be affixed by any one of a number of methods such as, for example, by gluing or by being slip-fit, so that no fluid leaks out. Infusion sleeve may be fabricated from any one of a number of materials such as, for example, metal or plastic, and may be molded, formed and so forth. Infusion tube 1110 is affixed at one end to infusion sleeve 1100 and at the other end to a source of liquid such as sterile water, not shown. Further, infusion sleeve contains apertures such as aperture 1120 disposed about infusion sleeve 1100.

In operation, fluids enter the eye from aperture 1120 to equalize the pressure therein. Then the vacuum applied to aperture 720 of outer needle 700 draws tissue and liquid into outer needle 700. As a result, the liquids help equalize the pressure in the eye and help transport cut tissue through the inventive apparatus.

Figure 11:
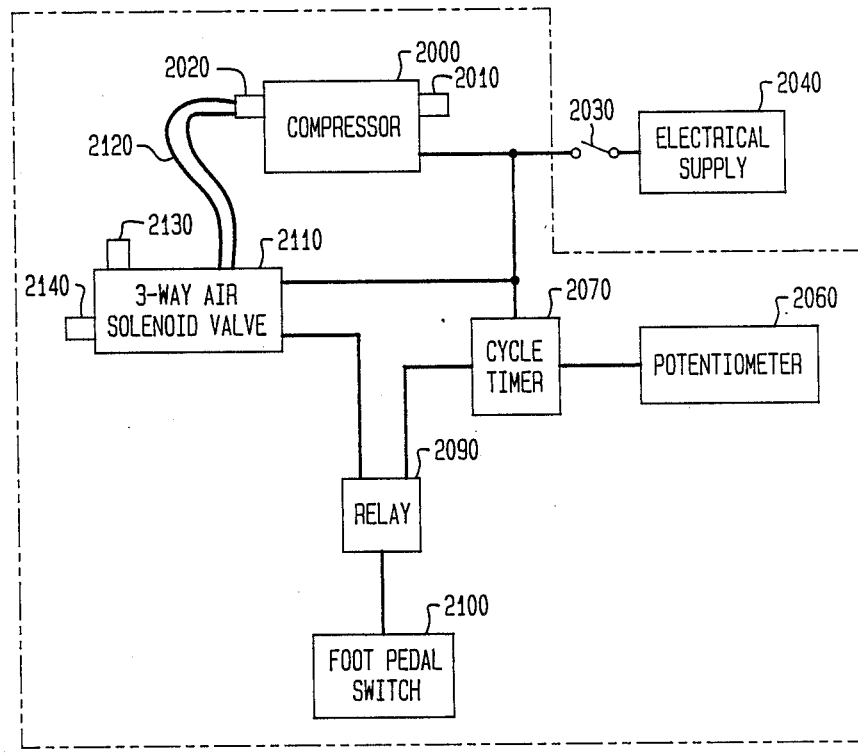
FIG. 11 shows, in pictorial form, an embodiment of an apparatus which provides compressed air pulses for use with embodiments of the present invention.

FIG. 11 shows, in pictorial form, an embodiment of an apparatus which provides compressed air pulses for use with embodiments of the present invention. Compressor 2000 inputs air through air-input-port 2010 and outputs compressed air through air-output-port 2020. Compressor 2000 may be any one of a number of commercially available apparatus such as, for example, a diaphragm pump, a piston pump, a rotary vane pump and so forth, and is activated by electrical supply 2040 through switch 2030. Electrical supply 2040 may be a commonly available 110 volt AC supply.

Cycle timer 2070 is connected to electrical supply 2040 through switch 2030 and outputs electrical pulses in responsa thereto, the rate of the electrical pulses output by cycle timer 2070 being adjusted by adjusting the setting of potentiometer 2060. The electrical pulses output by cycle timer 2070 are applied as input to 3-way air-solenoid valve 2110. Further, the output of electrical pulses from cycle timer 2070 is controlled by relay 2090 which is connected to cycle timer 2070 and to 3-way air-solenoid 2110. Relay 2090 is controlled, in turn, by foot pedal switch 2100, for example, a 5 volt DC switch. As a result, electrical pulses are applied to air-solenoid valve 2110 whenever foot pedal switch 2100 is depressed.

In response to electrical pulses applied to 3-way air-solenoid valve 2110 from cycle timer 2070 and the compressed air applied thereto from compressor 2000, 3-way air-solenoid valve 2110 outputs pulses of compressed air through outlet 2140 and allows air to be vented through air-release vent 2130 between pulses.

In operation, a surgeon connects air-intake-tube 180 from the embodiment shown in FIG. 1 to outlet 2140. Then, switch 2030 is turned on, potentiometer 2060 is set to the value which provides a desired pulse rate and foot pedal switch 2100 is depressed to provide pulses of compressed air for use with the inventive apparatus. It should be well known to those of ordinary skill in the art that many different models of appropriate cycle timers, 3-way air-solenoid valves, relays, and foot pedal switches are commercially available for use in fabricating the apparatus shown in FIG. 11.

Figure 12:
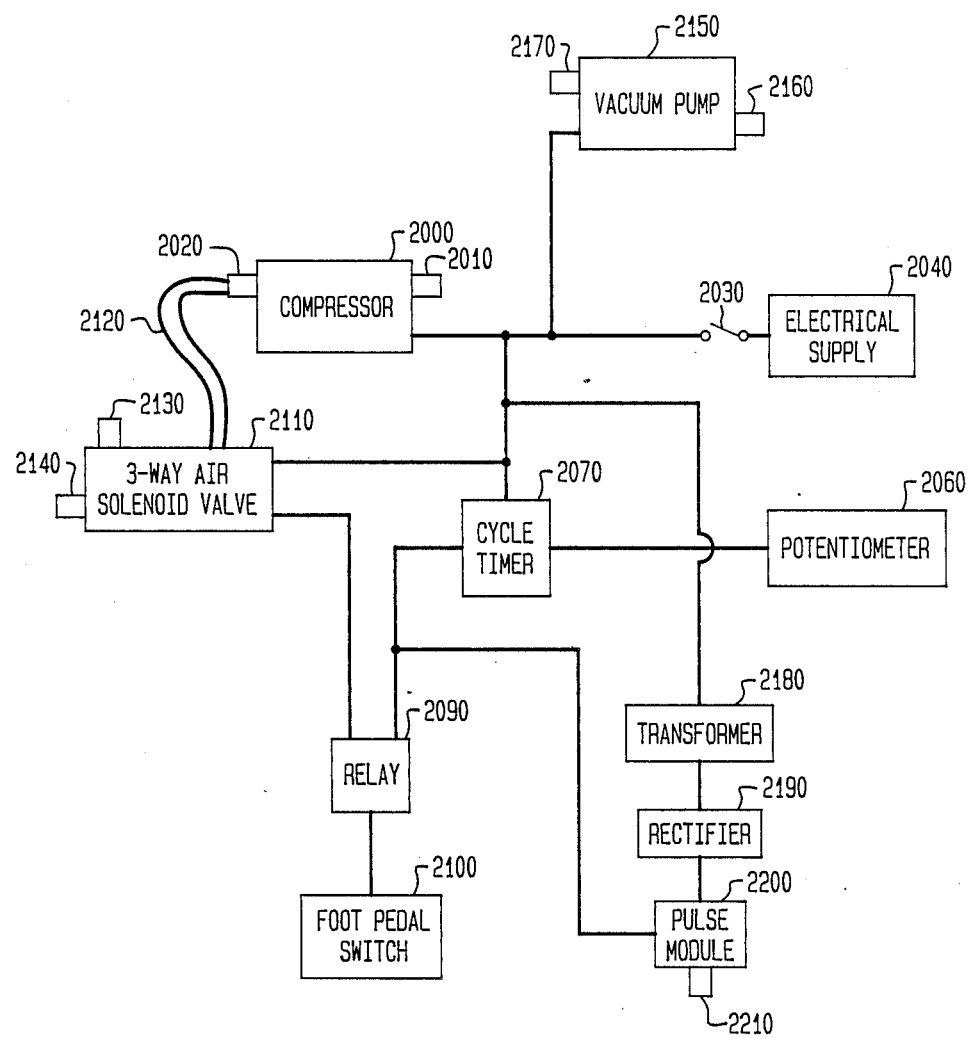
FIG. 12 shows, in pictorial form, an embodiment of an apparatus for providing compressed air pulses, a vacuum and/or electrical pulses for use with embodiments of the present invention.

FIG. 12 shows, in pictorial form, an embodiment of an apparatus for providing compressed air pulses, a vacuum and/or electrical pulses for use with embodiments of the present invention. In particular, the embodiment shown in FIG. 12 includes the apparatus shown in FIG. 11 and contains several additional components. First, FIG. 12 includes vacuum pump 2150 which has vacuum outlet 2160 and vent 2170. Vacuum pump 2150 is supplied with electrical voltage and current from electrical supply 2040 which is connected to vacuum pump 2150 through switch 2030. Second, a supply of electrical pulses for use with the embodiments shown in FIGS. 4-6 is provided by converting the 110 AC voltage available from electrical supply 2040 to a lower value, for example, 14 volts by transformer 2180. The output from transformer 2180 is converted to DC by rectifier 2190 and, in turn, is converted to DC pulses by pulse module 2200 at a rate which is determined by cycle timer 2070. The electrical pulses are output from pulse module 2200 at jack 2210.

In practice, the particular arrangement of the components of the apparatus shown in FIG. 12 may advantageously be such as to take advantage of commercially available modules. For example, I have modified a vacuum pump module available from Site Microsurgical Systems Inc. ("Site") and added compressor 2000 and 3-way air-solenoid valve 2110 thereto. Then I provided a connection between outlet 2140 of 3-way air-solenoid valve 2110 and an existing Site electrical power module which powers a Site vitrectomy apparatus. Lastly, I added all the remaining components shown in FIG. 12 thereto. In this manner, the existing Site electrical power module can supply air power to my inventive air-powered apparatus and electrical power either to Site's module or to my inventive electromagnetically-powered apparatus.

Figure 13:
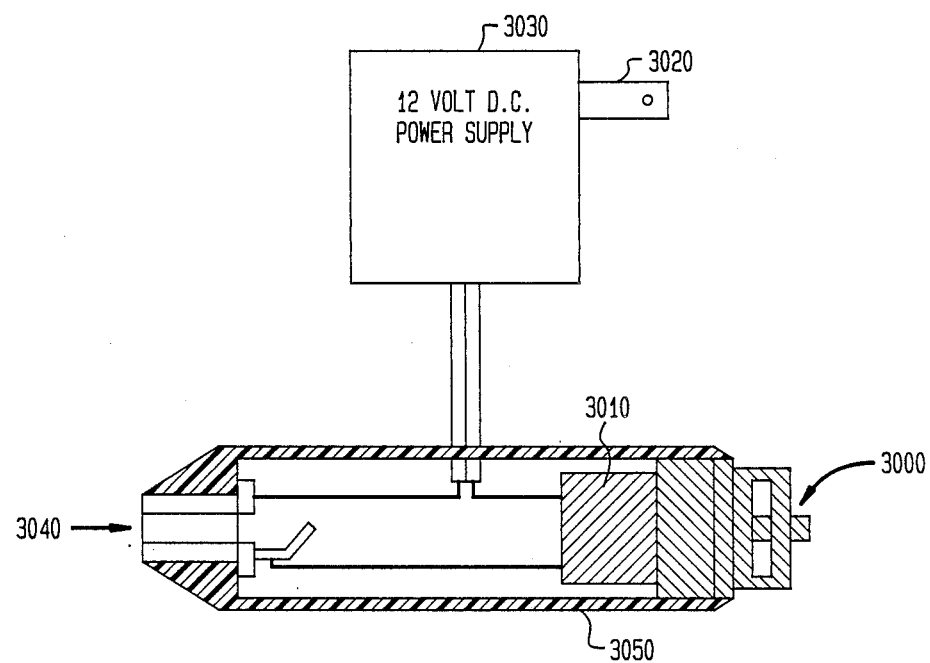
FIG. 13 shows, in pictorial, an embodiment of an apparatus for converting pulses of compressed air into electrical pulses for use with embodiments of the present invention.

FIG. 13 shows, in pictorial, an embodiment of an apparatus for converting pulses of compressed air which may be used, for example, to power the inventive apparatus shown in FIG. 1, into electrical pulses to power the inventive apparatus shown in FIGS. 4-6. Jack 3000 is affixed to chamber 3050 and is connected to a source of pulses of compressed air. The pulses of compressed air input to jack 3000 are applied to pressure switch 3010 disposed in chamber 3050. Jack 3020 is connected to a standard source of electrical voltage, for example, 110 volts AC, and applies this voltage to 12 volt power supply 3030. Further, the output from pressure switch 3010 is also applied to power supply 3030. As a result, power supply 3030 produces 12 volt DC pulses which are applied to output jack 3040 disposed in chamber 3050. These pulses are then used to drive the inventive apparatus shown in FIGS. 4-6. Power supply 3030 could be any input or output voltage.

Although particular embodiments of the present invention have been shown and described herein, many varied embodiments incorporating the teachings of the present invention may be constructed by those skilled in the art. It should ba clear that the means for adjusting the maximum opening in the size of the sidewall of the outer needle shown in FIG. 3 may be used in all embodiments. Further, although the embodiments show the use of a spring means for driving the inner tube such in a direction as to open the aperture formed in the sidewall of the outer needle, other means may be used such as, for example, the application of compressed liquid or gas in the opposite direction from the drive means in the first direction. Further, it should be clear to those of ordinary skill in the art that the above-described embodiments are not restricted to use in removing vitreous from an eye. In fact, they may he used in a wide variety of applications such as, for example, removing polyps, brain surgery, cardio-vascular surgery and so forth.

What is claimed is:

1. A surgical apparatus for removing tissue which comprises:
 a first tube having an aperture in a sidewall;

a second tube having at least one portion disposed within the first tube and having a sharp end and another end for applying a vacuum thereto;
an electromagnetic drive means for reciprocating the second tube within the first tube so that at least a portion of the sharp end of the second tube moves across the aperture to thereby cut tissue which extends through the aperture, the electromagnetic means comprising:
 (a) a chamber;
 (b) generating means, disposed within the chamber, for providing a magnetic field in response to the application of electrical current thereto;
 (c) magnetic means, affixed to the second tube and being disposed in the chamber, the magnetic means being attracted by the magnetic, field for moving in a first direction when the magnetic field is generated;
 (d) the generating means and the magnetic means being further comprised of indexing means for inhibiting rotation of the magnetic means with respect to the generating means and, thereby, for inhibiting rotation of the second tube with respect to the first tube; and
 (e) the chamber being further comprised of venting means for releasing air trapped in the chamber;
adjusting means for adjusting the distance of movement of the magnetic means and, thereby, the distance of the movement of the second tube, whereby the opening of the aperture into which the tissue enters the first tube is varied;
said generating means comprises a bobbin having wires wrapped therearound and a passageway disposed therethrough; and
said magnetic means is comprised of a material which is attracted by the magnetic field and the magnetic means has a cross-section whose dimensions are smaller than the dimensions of a cross section of the passageway;
a retaining means, affixed to one end of the magnetic means, and a tension means, disposed between the bobbin and the retaining means, for driving the retaining means and, thereby, the magnetic in a second direction, and
said indexing means comprises guide means, affixed to the bobbin, having a passageway disposed therein and having a groove extending along a portion of the surface of the passageway and a extending means, affixed to the magnetic, disposed to extend into the groove.

2. The surgical apparatus of claim 1 which further comprises an energy absorbing means affixed to the guide means for absorbing energy whenever the retaining means impacts thereon.

3. The surgical apparatus of claim 1 wherein the guide means is comprised of an energy absorbing material.

4. The surgical apparatus of claim 1 wherein the aperture is elliptical in shape.

5. The surgical apparatus of claim 1 wherein the wires wrapped around the bobbin are electrically connected together in parallel.

6. A surgical apparatus for removing tissue which comprises
a first tube having an aperture in a sidewall;
a second tube having at least one portion disposed within the first tube and having a sharp end and another end for applying a vacuum thereto;
an electromagnetic drive means for reciprocating the second tube within the first tube so that at least a portion of the sharp end of the second tube moves across the aperture to thereby cut tissue which extends through the aperture, the electromagnetic means comprising:
 (a) a chamber;
 (b) generating means, disposed within the chamber, for providing a magnetic field in response to the application of electrical current thereto;
 (c) magnetic means, affixed to the second tube and being disposed in the chamber, the magnetic means being attracted by the magnetic field, for moving in a first direction when the magnetic field is generated;
 (d) the generating means and the magnetic means being further comprised of indexing means for inhibiting rotation of the magnetic means with respect to the generating means and, thereby, for inhibiting rotation of the second tube with respect to the first tube; and
 (e) the chamber being further comprised of venting means for releasing air trapped in the chamber;
adjusting means for adjusting the distance of movement of the magnetic means and, thereby, the distance of the movement of the second tube, whereby the opening of the aperture into which the tissue enters the first tube is varied;
said generating means comprises a bobbin having wires wrapped therearound and a passageway disposed therethrough; and
said magnetic means is comprised of a material which is attracted by the magnetic field and the magnetic means has a cross-section whose dimensions are smaller than the dimensions of a cross section of the passageway;
a retaining means, affixed to one end of the magnetic means, and a tension means, disposed between the bobbin and the retaining means, for driving the retaining means and, thereby, the magnetic means in a second direction, and
said indexing means comprises the shape of a cross-section of the passageway being substantially non-circular and the shape of a cross-section of the outer surface of the magnetic means being substantially the same.

7. A surgical apparatus for removing tissue which comprises:
a first tube having an aperture in a sidewall;
a second tube having at least one portion disposed within the first tube and having a sharp end and another end for applying a vacuum thereto;
an electromagnetic drive means for reciprocating the second tube within the first tube so that at least a portion of the sharp end of the second tube moves across the aperture to thereby cut tissue which extends through the aperture, the electromagnetic means comprising:
a chamber;
 (b) generating means, disposed within the chamber, for providing a magnetic field in response to the application of electrical current thereto;
magnetic means, affixed to the second tube and being disposed in the chamber, the magnetic means being attracted by the magnetic field, for moving in a first direction when the magnetic field is generated;

(d) the generating means and the magnetic means being further comprised of indexing means for inhibiting rotation of the magnetic means with respect to the generating means and, thereby, for inhibiting rotation of the second tube with respect to the first tube; and (e) the chamber being further comprised of venting means for releasing air trapped in the chamber;

adjusting means for adjusting the distance of movement of the magnetic means and, thereby the distance of the movement of the second tube, whereby the opening of the aperture into which tissue enters the first tube is varied;

said generating means comprises a bobbin having wires wrapped therearound;

said magnetic means is comprised of a material which is attracted by the magnetic field and the magnetic means has a cross-section whose dimensions are larger than the dimensions of a cross-section of any passageway in the bobbin;

a retaining means affixed to one end of the magnetic means, a tension means disposed between the bobbin and the retaining means for driving the retaining means and thereby the magnetic means in a second direction, and an impact neutralizer means for absorbing energy from the magnetic means; and wherein the indexing means comprises a member extending from the bobbin into an aperture in the retaining means.

8. A surgical apparatus for removing tissue which comprises:

a first tube having an aperture in a sidewall;

a second tube having at least one portion disposed within the first tube and having a sharp end and another end for applying a vacuum thereto;

an electromagnetic drive means for reciprocating the second tube within the first tube so that at least a portion of the sharp end of the second tube moves across the aperture to thereby cut tissue which extends through the aperture, the electromagnetic means comprising:

(a) a chamber;

(b) generating means, disposed within the chamber, for providing a magnetic field in response to the application of electrical current thereto;

magnetic means, affixed to the second tube and being disposed in the chamber, the magnetic means being attracted by the magnetic field, for moving in a first direction when the magnetic field is generated;

(d) the generating means and the magnetic means being further comprised of indexing means for inhibiting rotation of the magnetic means with respect to the generating means and, thereby, for inhibiting rotation of the second tube with respect to the first tube; and (e) the chamber being further comprised of venting means for releasing air trapped in the chamber;

adjusting means for adjusting the distance of movement of the magnetic means and, thereby, the distance of the movement of the second tube, whereby the opening of the aperture into which tissue enters the first tube is varied;

said generating means comprises a bobbin having wires wrapped therearound;

said magnetic means is comprised of a material which is attracted by the magnetic field and the magnetic means has a cross-section whose dimensions are larger than the dimensions of a cross-section of a passageway disposed through the bobbin;

a retaining means affixed to one end of the magnetic means, a tension means disposed between the bobbin and the retaining means for driving the retaining means and, thereby, the magnetic means in a second direction, and an impact neutralizer means for absorbing energy from the magnetic means; and wherein the indexing means comprises guide means, affixed to the magnetic means, having a first outer shape which is substantially the same as the shape of the cross-section of the passageway, which shape is substantially non-circular.

* * * * *